US012788614B2

(12) United States Patent
Jones et al.

(10) Patent No.: US 12,788,614 B2
(45) Date of Patent: Nov. 10, 2026

(54) COUPLING SYSTEM FOR OSTOMY APPLIANCES

(71) Applicant: CONVATEC TECHNOLOGIES INC., Las Vegas, NV (US)

(72) Inventors: Don Jones, Stokesdale, NC (US); Mark E. Martich, Greensboro, NC (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 241 days.

(21) Appl. No.: 18/815,785

(22) Filed: Aug. 26, 2024

(65) Prior Publication Data

US 2024/0415690 A1 Dec. 19, 2024

Related U.S. Application Data

(60) Division of application No. 17/564,981, filed on Dec. 29, 2021, now Pat. No. 12,070,410, which is a continuation of application No. PCT/US2021/065482, filed on Dec. 29, 2021.

(60) Provisional application No. 63/132,806, filed on Dec. 31, 2020.

(51) Int. Cl.

| | |
|---|---|
| ***A61F 5/443*** | (2006.01) |
| ***A61F 5/448*** | (2006.01) |
| ***B29C 45/14*** | (2006.01) |
| *B29L 31/00* | (2006.01) |

(52) U.S. Cl.
CPC .............. *A61F 5/443* (2013.01); *A61F 5/448* (2013.01); *B29C 45/14467* (2013.01); *B29L 2031/7148* (2013.01)

(58) Field of Classification Search
CPC .... A61F 5/443; A61F 5/448; B29C 45/14467; B29L 2031/7148
See application file for complete search history.

(56) References Cited

U.S. PATENT DOCUMENTS

| | | | | |
|---|---|---|---|---|
| 2,684,676 A * | 7/1954 | Perry | ...................... | A61F 5/445 604/344 |
| 2,818,069 A | 12/1957 | Fenton | | |
| 3,021,843 A | 2/1962 | Perry | | |
| 3,495,592 A | 2/1970 | Shepard | | |
| 3,528,420 A | 9/1970 | Nielsen | | |

(Continued)

FOREIGN PATENT DOCUMENTS

| | | |
|---|---|---|
| EP | 3955864 A1 | 2/2022 |
| EP | 3958801 A1 | 3/2022 |

(Continued)

OTHER PUBLICATIONS

EP Examination Report; European Patent Office; EP Patent Application 21916404.3; Dated Jul. 29, 2025; 4 pages.

(Continued)

*Primary Examiner* — Guy K Townsend
(74) *Attorney, Agent, or Firm* — TAFT STETTINIUS HOLLISTER LLP; Ryan O. White; Derek B. Lavender

(57) ABSTRACT

A coupling assembly for an ostomy appliance that has a bag side flange having a bag and an integrated element having an accordion membrane and a body side flange, the integrated element configured to be selectively coupled to the bag side flange. The integrated element is formed in a single manufacturing process.

11 Claims, 9 Drawing Sheets

DETAIL B

(56) References Cited

U.S. PATENT DOCUMENTS 3,878,847 A 4/1975 Marsan
4,095,599 A 6/1978 Simonet Haibe
4,219,023 A 8/1980 Galindo
4,419,100 A * 12/1983 Alexander .............. A61F 5/448 604/339
4,460,363 A 7/1984 Steer et al.
4,559,048 A 12/1985 Steer
4,610,676 A 9/1986 Schneider et al.
4,664,661 A * 5/1987 Ferguson ................ A61F 5/448 604/344
4,775,374 A 10/1988 Cilento et al.
4,816,023 A 3/1989 Freeman
4,826,496 A * 5/1989 Ferguson ................ A61F 5/448 604/339
4,828,553 A 5/1989 Nielsen
4,846,820 A * 7/1989 Jensen .................... A61F 5/445 604/339
4,850,985 A 7/1989 Edwards et al.
4,872,869 A 10/1989 Johns
4,883,477 A 11/1989 Steer
4,950,261 A 8/1990 Steer
4,973,324 A 11/1990 Steer
5,004,464 A 4/1991 Leise, Jr.
5,074,852 A 12/1991 Castellana et al.
5,160,330 A 11/1992 Cross
5,178,615 A 1/1993 Steer et al.
5,185,008 A 2/1993 Lavender
5,257,981 A 11/1993 Takahashi
5,269,773 A 12/1993 Vidal
5,312,381 A 5/1994 Brooks
5,312,382 A * 5/1994 Metz ....................... A61F 5/448 604/338
5,322,523 A 6/1994 Olsen
5,330,454 A * 7/1994 Klingler .................. A61F 5/448 604/338
5,330,455 A 7/1994 McKay
5,346,482 A * 9/1994 Metz ....................... A61F 5/448 604/338
5,429,625 A 7/1995 Holmberg
5,496,297 A 3/1996 Olsen
5,501,677 A 3/1996 Jensen
5,520,670 A 5/1996 Blum
5,607,413 A 3/1997 Holmberg et al.
5,662,628 A 9/1997 Hollands
5,709,674 A 1/1998 Steer
5,730,735 A 3/1998 Holmberg et al.
5,814,033 A 9/1998 Edwards
5,947,941 A 9/1999 Leise, Jr. et al.
6,071,268 A 6/2000 Wagner
6,106,507 A * 8/2000 Botten .................... A61F 5/448 604/338
6,106,508 A 8/2000 Lavender
6,210,384 B1 4/2001 Cline
6,293,930 B1 9/2001 Brunsgaard et al.
6,520,943 B1 2/2003 Wagner
7,087,042 B2 8/2006 Montgomery
7,192,420 B2 3/2007 Whiteford
8,211,073 B2 * 7/2012 Dove ...................... A61F 5/445 604/338
8,336,695 B2 12/2012 Kataoka et al.
8,366,695 B2 * 2/2013 Foley ...................... A61F 5/448 604/338
8,449,513 B2 5/2013 Abrams
9,402,761 B2 8/2016 Argent
9,517,158 B2 * 12/2016 Masters .................. A61F 5/448
9,707,120 B2 7/2017 Nguyen-DeMary et al.
10,335,309 B2 * 7/2019 Becker .................... A61F 5/445
10,456,289 B2 10/2019 Alden et al.
10,512,562 B2 * 12/2019 Kavanagh ............... A61F 5/448
11,051,971 B2 7/2021 Schertiger
11,135,084 B2 10/2021 Seres et al.
11,148,845 B1 10/2021 Ellis
11,219,547 B2 1/2022 Schertiger et al.
11,291,577 B2 4/2022 Seres et al.
11,291,579 B2 4/2022 Hanuka et al.
11,690,752 B2 7/2023 Nyberg et al.
11,737,906 B2 * 8/2023 Jones ...................... A61F 5/443 604/342
11,806,267 B2 11/2023 Seres et al.
2001/0004687 A1 6/2001 Plass et al.
2004/0039357 A1 2/2004 Andersen
2007/0027434 A1 * 2/2007 Pedersen ................. A61F 5/441 604/338
2010/0241092 A1 9/2010 Nguyen-DeMary et al.
2012/0059341 A1 * 3/2012 Masters .................. A61F 5/448 604/339
2012/0165767 A1 6/2012 Abrams
2015/0297389 A1 10/2015 Nyberg
2015/0359658 A1 12/2015 Leise, Jr.
2016/0302959 A1 * 10/2016 Kavanagh ............... A61F 5/449
2019/0254863 A1 8/2019 Alden et al.
2020/0253777 A1 * 8/2020 Jones ...................... A61F 5/443
2022/0031495 A1 2/2022 Seres et al.
2022/0192860 A1 6/2022 Hansen et al.
2022/0202606 A1 * 6/2022 Jones ........................ A61F 5/44
2023/0240882 A1 8/2023 Seres et al.
2023/0255814 A1 8/2023 Donovan et al.
2023/0263652 A1 8/2023 Donovan et al.

FOREIGN PATENT DOCUMENTS

EP 3755285 B1 5/2022
EP 4008296 A1 6/2022
EP 4228564 A1 8/2023
EP 3755284 B1 10/2023
EP 3057544 B1 11/2023
WO 2022117357 A1 6/2022

OTHER PUBLICATIONS

CN Office Action; China National Intellectual Property Administration; CN Application No. 202180088476.3; dated Jul. 17, 2025; 17 pages.

* cited by examiner

DETAIL B

SECTION A-A

COUPLING SYSTEM FOR OSTOMY APPLIANCES

CROSS-REFERENCE TO RELATED APPLICATION

The present application is a divisional of U.S. application Ser. No. 17/564,981 filed Dec. 29, 2021, which is a bypass continuation of PCT Application No. PCT/US21/65482, filed 29 Dec. 2021, which claims the benefit of U.S. Provisional Patent Application No. 63/132,806 filed on Dec. 31, 2020, the contents of which are incorporated herein in entirety.

FIELD OF THE DISCLOSURE

The present invention relates to an ostomy coupling for removably attaching an ostomy appliance to a body fitment worn on the body of an ostomate and more specifically to providing a body fitment with a floatable coupling part.

BACKGROUND OF THE DISCLOSURE

The present disclosure relates to devices that attach to a patient's body after they have undergone a surgical ostomy procedure to address a problem with their gastrointestinal tract. The varied problems they experience interfere with their body's normal processes for processing and collecting the waste products from the digestive processes. Ostomates, as these patients are referred to, are typically required to wear and maintain these waste-collection devices for the remainder of their life. At their essence, the devices are typically comprised of an adhesive "doughnut" surrounding the stoma's exit from their abdomen. The adhesive adheres to the patient on one side and attaches to a collection bag on the other. The system is intended during operation to provide a liquid and reasonably gas-tight seal so the ostomate can enjoy an active and socially engaged life.

U.S. Pat. Nos. 4,419,100, 4,610,676, 4,610,677, 5,730,735, 5,312,382, 8,366,695 (hereinafter "the '695 Patent"), and U.S. Pat. No. 8,382,732 (hereinafter "the '732 Patent") teach an ostomy coupling designed to reduce discomfort that some ostomates experience as a result of an attachment force applied through the body fitment to the skin, when two coupling parts are pressed together. The problem of discomfort is especially important during post-operative care, when the stoma surgery is recent and the abdominal skin is very tender. These documents teach a flexible collar suspension permanently secured between the adhesive wafer and the coupling part of the body fitment. The flexible collar allows the coupling part to be displaced away from or "float" with respect to the adhesive wafer, at least by a sufficient amount for a user to insert one or more fingers behind the coupling part, in order to manually support the coupling part against the attachment force when the appliance is pressed against the body fitment. Such a coupling part is generally referred to in the art as being a floating coupling part.

Frequently, these ostomy devices are designed so that the collection bag can be detached from the adhesive via coupling flanges. This allows a fresh bag to be reattached without disturbing the underlying adhesive doughnut. This extends useable life of the adhesive, reducing cost, and minimizes skin irritation to the patient from more frequent adhesive changes. Commonly, products with this configuration are referred to as "two-piece" ostomy devices.

Another drawback to the typical designs is that the forces required to decouple and recouple the flanges are reacted directly back against the patient's abdomen. The '695 Patent and the '732 Patent teach two-piece ostomy devices designed to reduce the discomfort that many ostomates experience as a result of the attachment and detachment forces applied through the coupling.

The '695 design focuses on the period immediately following initial operative care when the wound is particularly swollen and sensitive. Doctors and post-operative staff are attending to the patient during this time. The coupling is fixed an extended distance away from the patient. This provides space for attending staff to easily support the coupling during detachment and reattachments, thereby isolating forces from the patient's abdomen.

The '732 Patent addresses the conditions found during the more common, normal, daily routine the patient experiences while wearing the collection appliance after the operative recovery period is over. The coupling can temporarily extend (or "float") via the flexible membrane. This improves access for maintenance care by allowing the space for the wearer to insert one or more fingers behind the coupling. The wearer can support and isolate the reaction forces from decoupling and recoupling the flanges. The coupling can then collapse back to a flat position for wearing, improving comfort and appearance under clothing. The '732 Patent describes a preferred embodiment where the coupling is in fact "bistable" (i.e. holding stable in the collapsed state to resist movement or sagging for active wearers and holding stable in the extended state while the wearer is manipulating the bag coupling).

In the typical two-piece ostomy device the body-side and bag-side coupling flanges are manufactured separately from the flexible membrane. The flexible membrane is then subsequently coupled to the body-side flange and bag-side flange. In typical two-piece device, the attachment of the flexible membrane to the body-side flange has proven problematic. More specifically, the extensible membrane is typically produced by first extruding a thin, flat, flexible film made from a polyethylene copolymer or the like. The film is rolled and subsequently fed into a vacuum thermoforming operation to achieve a folded "accordion" shape. The accordion shapes are then die-cut into individual components with the required inner and outer diameter dimensions. The copolymer used for extrusion is selected to optimize flexibility while still providing a stiff-enough structure to achieve bi-stability.

The thin-film extrusion is prone to potential inclusion of small air bubbles and foreign particulate, resulting in pinholes through the film. This requires careful process control. The thermoforming process is inherently unable to control wall thickness, resulting in particularly thin walls where the film is required to stretch the most. These two factors combine to give rise to intermittently occurring small holes through the membrane that are only detectable after a subassembly has been produced and leak tested.

The body-side flange and the accordion membrane are brought together and joined with a heat-welding operation to create a subassembly for further processing into finished product. Handling the thin membrane with automated assembly equipment and placing the membrane precisely concentric with the flange prior to welding has proven challenging. The subsequent welding operation and in-process leak and dimensional testing have all combined to be the source of significant, non-recoverable scrap.

The present disclosure addresses these issues, among others, that are problematic in the prior art.

SUMMARY

The present disclosure integrates the body-side flange and the accordion membrane into a single part that may be formed through injection molding. This eliminates the expense and complications of producing a separate, thin-wall membrane from extruded film and then thermoforming and die cutting the film to produce an accordion membrane component. This disclosure also provides for a more efficient manufacturing process that improves on the prior art process of bringing the membrane together with a separate flange and joining them together.

Using an injection-molding process to produce the flexible portion allows wide design latitude. Unlike the film extrusion process where wall thickness must be kept uniform, wall thickness can be optimized for different sizes of products and can be further optimized within a given product size. For example, thicker sectional areas can be provided where stiffness is desired and thinner ones where flexibility is needed.

One embodiment of this disclosure is a coupling assembly for an ostomy appliance that has a bag side flange having a bag and an integrated element having an accordion membrane and a body side flange, the integrated element is configured to be selectively coupled to the bag side flange. The integrated element is formed in a single manufacturing process.

In one example of this embodiment the single manufacturing process is an injection molding process.

In another example, the integrated element defines deflectable seal configured to seal the integrated element to the bag side flange when coupled to one another. In part of this example, the deflectable seal connects the accordion membrane to the body side flange. In one aspect of this part, the deflectable seal has a first thickness at a base portion and a second thickness at a scaling portion, the second thickness being less than the first thickness. The deflectable seal transitions to the accordion membrane through the sealing portion. Further, the accordion membrane has a third thickness, the third thickness being less than the first and second thickness. In an alternative configuration, the accordion membrane has a third thickness, the third thickness being substantially the same as the second thickness.

In another example, the integrated element comprises a bridging ring section that is coupled to a bridging ring, the bridging ring configured to be coupled to an abdominal wall of a patient with an adhesive about a stoma. In part of this example, the integrated element is coupled to the bridging ring via a weld and the weld between the bridging ring and the integrated element is the only weld on the integrated element.

Another embodiment is a process for manufacturing a coupling assembly for an ostomy appliance. The process includes having a mold to form an integrated element having a bridging ring section, an accordion membrane, and a body side flange, injecting a material into the mold to form the integrated element in a single injection process, and removing the integrated element from the mold. The integrated element is configured so the accordion membrane is deformable to allow the body side flange to transition between a retracted position and an extended position relative to the bridging ring section.

One example of this embodiment includes welding the integrated element to a bridging ring. Part of this example includes coupling an adhesive to the bridging ring, the adhesive configured to allow a user to selectively couple the bridging ring and corresponding integrated component to the user's abdomen wall.

Another example of this embodiment includes forming a deflectable seal into the integrated element as part of the single injection process. The deflectable seal has a base section having a first thickness and a sealing portion with a second thickness that is less than the first thickness. Further, the accordion membrane has a third thickness that is different from the first and second thickness.

Yet another example of this embodiment includes forming a locking shelf into the integrated element during the single injection process.

Another embodiment of this disclosure is a method for making a coupling assembly for an ostomy appliance. The method includes providing a bag side flange configured to be selectively coupled to a deflectable seal about a stoma and forming an integrated element from a single material, the integrated element having a bridging ring section, an accordion membrane, a body side flange and defining the deflectable seal. In this embodiment, the integrated element is configured to selectively couple the bag side flange to the deflectable seal of the integrated element so the accordion membrane is deformable to allow the body side flange to transition between a retracted position and an extended position relative to the bridging ring section.

One example of this embodiment includes coupling the integrated element to a bridging ring configured to be selectively coupled to a user. This example may include coupling an adhesive to the bridging ring, the adhesive configured to allow a user to selectively couple the bridging ring and corresponding integrated component to the user's abdomen wall. Another example of this embodiment includes forming a locking shelf into the integrated element during the single injection process.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein.

DETAILED DESCRIPTION

The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure.

Figure 1C:
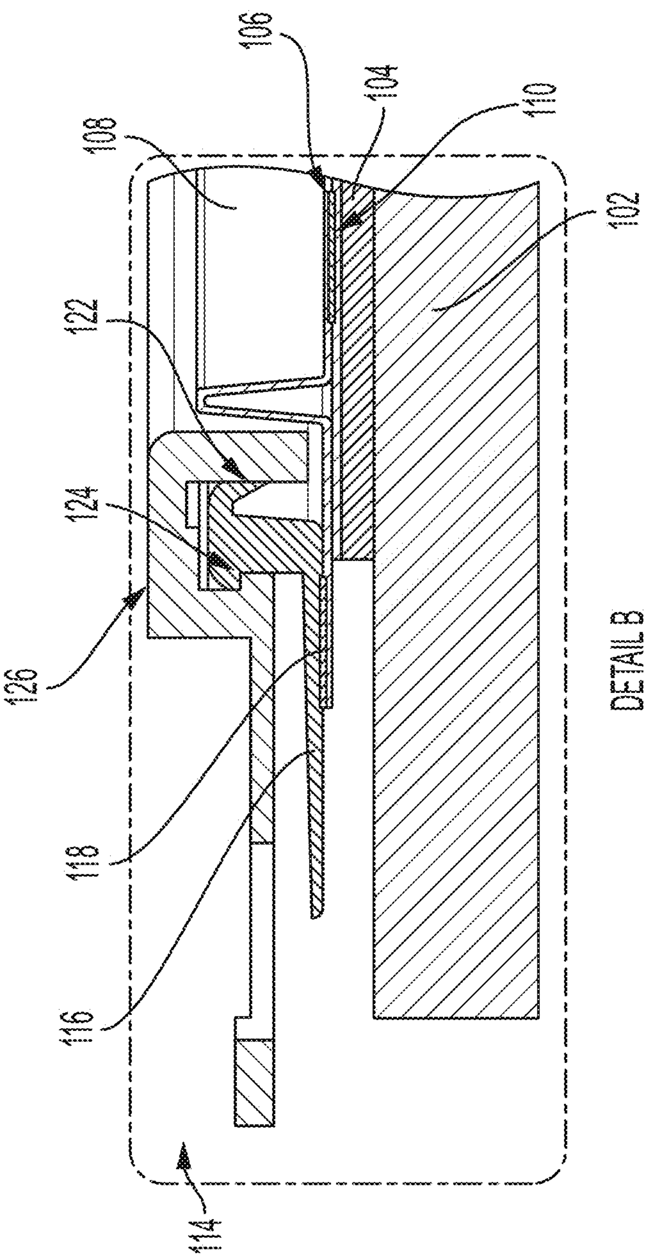
FIG. 1*c* is a detailed view of the cross-sectional view of FIG. 1*b;*
Figure 1A:
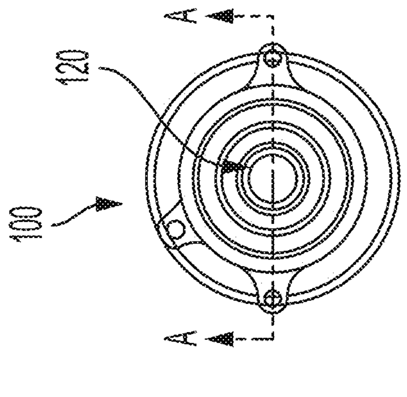
FIG. 1*a* is a top view of one embodiment of a coupling assembly for a two-piece ostomy appliance in a retracted position.
Figure 1B:
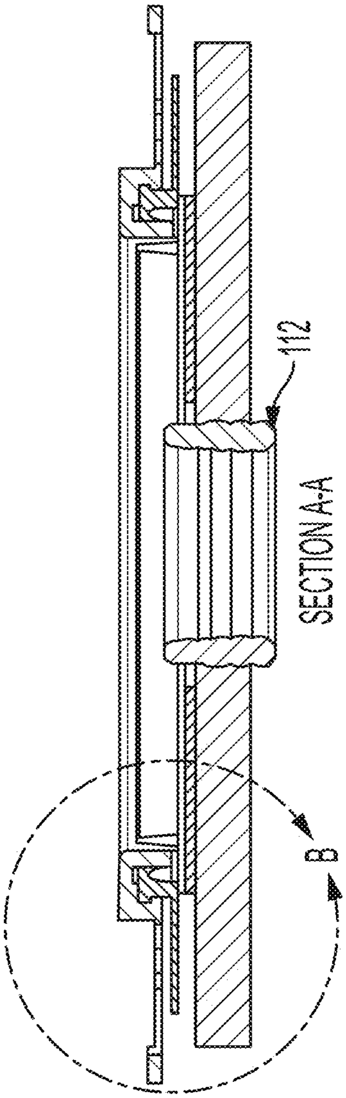
FIG. 1*b* is a cross-sectional view of the coupling assembly of FIG. 1*a;*

FIGS. 1*a*-1*c* illustrate a coupling assembly 100 for a two-piece ostomy appliance. The coupling assembly 100 may be selectively coupled to a patient's abdomen wall 102 via an adhesive 104 or the like. More specifically, a bridging ring 106 may be coupled to the adhesive 104 on one side and welded or otherwise coupled to an accordion membrane 108 on the other. The bridging ring 106 may be coupled to the accordion membrane 108 along a weld area 110 that couples the accordion membrane 108 to the bridging ring substantially entirely around an opening 120 that is configured to be positioned around a stoma 112. The accordion membrane 106 may be coupled to the bridging ring 106 along the weld area 110 to substantially prevent fluid from passing from the stoma 112 through the weld area 110 to a surrounding environment 114 when coupled to the abdomen wall 102.

In the embodiment of FIGS. 1*a*-1*c* and 2*a*-2*c*, a body side flange 116 may also be coupled to a portion of the accordion membrane 108. The body side flange 116 may be coupled to the accordion membrane 108 along a weld area 118 that is radially away from the weld area 110 relative to the opening 120. The weld area 118 may also extend entirely around the opening 120 to substantially prevent fluid from passing from the stoma 112 to the surrounding environment when a bag is coupled thereto.

Figure 2C:
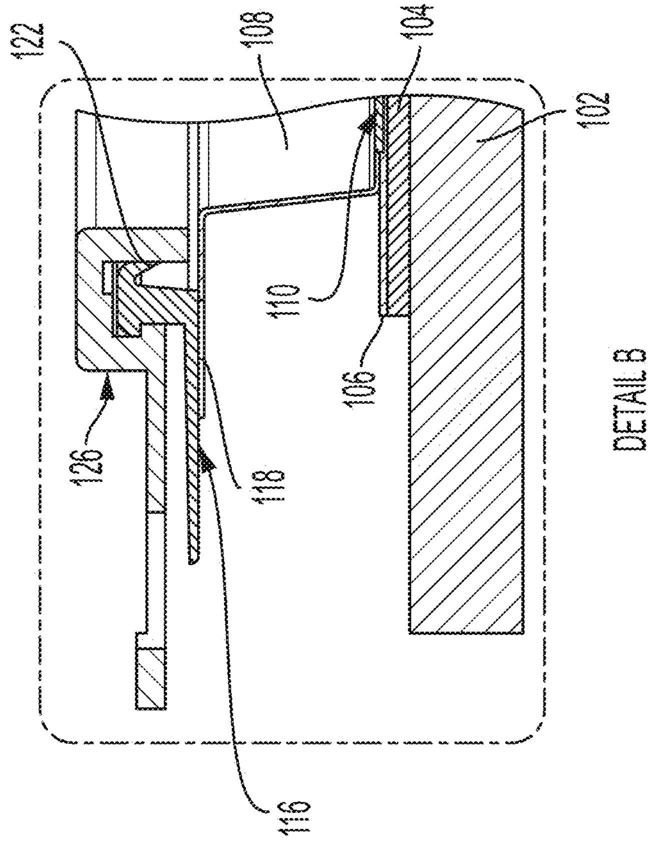
FIG. 2*c* is a detailed view of the cross-sectional view of FIG. 2*b;*
Figure 2A:
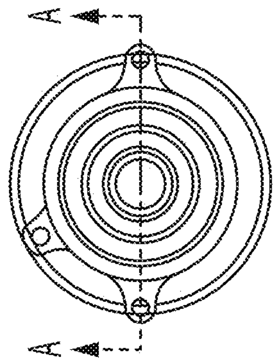
FIG. 2*a* is a top view of the coupling assembly of FIG. 1*a* in an extended position.
Figure 2B:
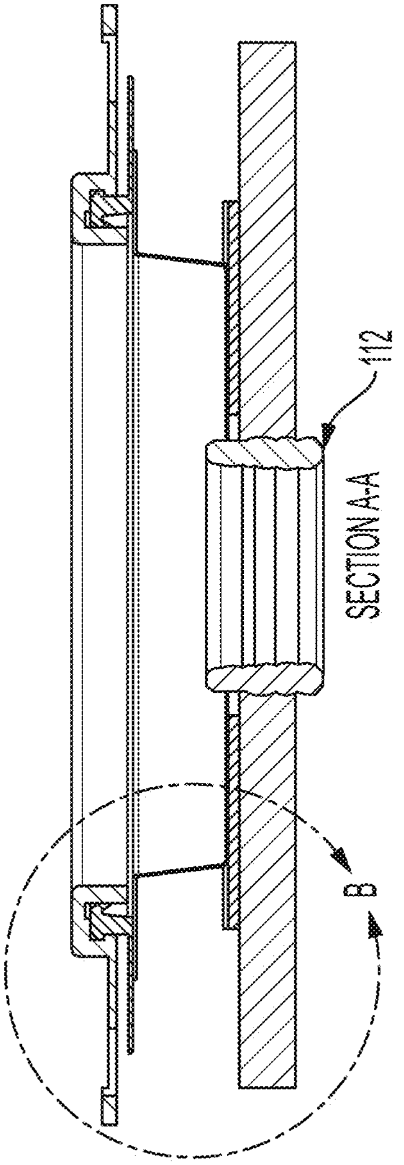
FIG. 2*b* is a cross-sectional view of the coupling assembly of FIG. 2*a;*
Figure 3C:
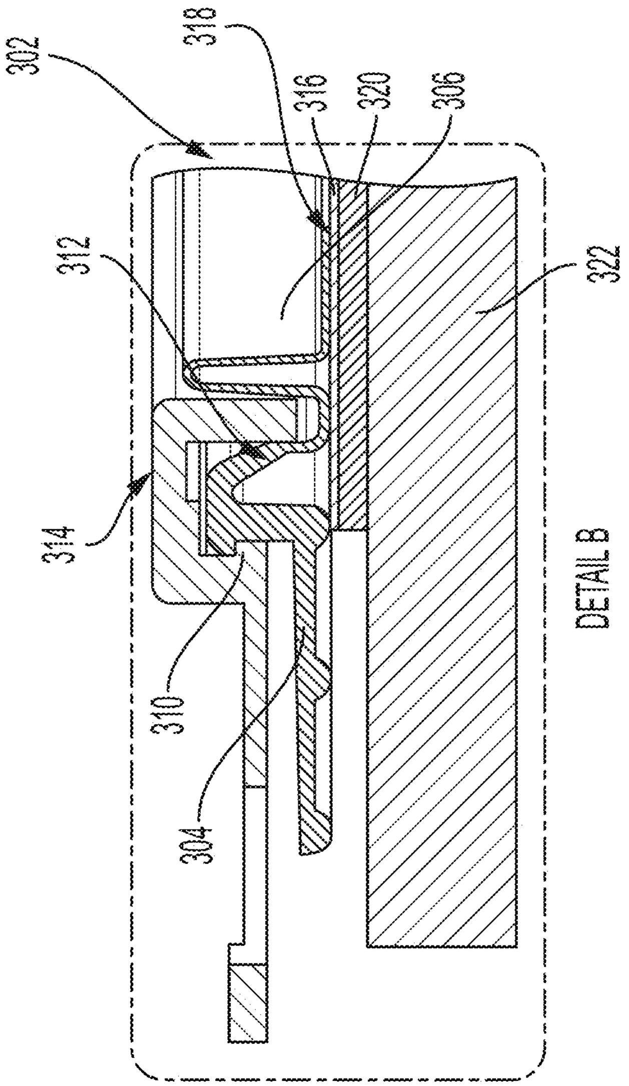
FIG. 3*c* is a detailed view from the cross-sectional view of FIG. 3*b;*
Figure 3A:
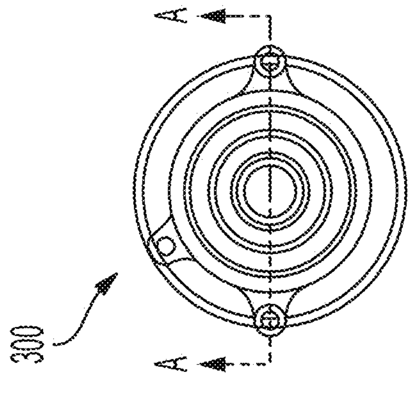
FIG. 3*a* is a top view of one embodiment of an improved coupling assembly for a two-piece ostomy appliance in a retracted position.
Figure 3B:
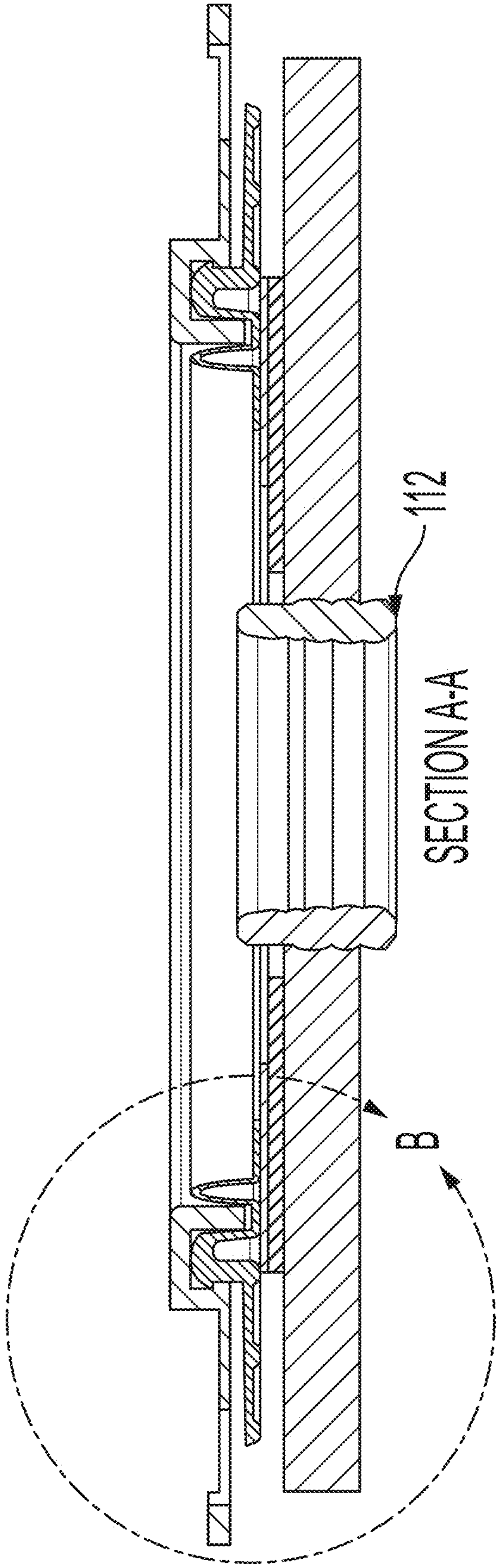
FIG. 3*b* is a cross-sectional view of the coupling assembly of FIG. 3*a;*

In one aspect of this embodiment, the accordion membrane 108 has at least one fold between the bridging ring 106 and the body side flange 116 that allows the body side flange 116 to extend therefrom between the retracted position of FIGS. 1*a*-1*c* and the extended position of FIGS. 2*a*-2*c*. The retracted position of FIGS. 1*a*-1*c* may be to allow the ostomy appliance to lay as close to the abdomen wall 102 as possible during normal use. The extended position of FIGS. 2*a*-2*c* may be intended to provide a user access to the coupling assembly 100 to easily couple and uncouple the corresponding ostomy bag.

The body side flange 116 may also have a deflectable seal 122 and a locking shelf 124 defined about a circumference of the body side flange 116. The locking shelf 124 and deflectable seal 122 may correspond with a bag side flange 126 to selectively couple the bag side flange 126 to the body side flange 116. More specifically, the locking shelf 124 may be positioned along a radially outer portion of the body side flange 116 relative to the seal 122 and have an angled leading surface and a trailing locking surface. The bag side flange 126 may typically have a corresponding bag coupled around the opening 120 to substantially contain effluent from the stoma 112 when coupled to body side flange 116.

When the bag side flange 126 is being coupled to the body side flange 116, the angled leading surface is aligned with a corresponding recess in the bag side flange 126 and the flanges 116, 126 may be transitioned towards one another. As the flanges 116, 126 become aligned as illustrated in FIG. 1, the angled leading surface deflects radially inwardly until the trailing locking surface is fully positioned in the recess of the bag side flange 126. The recess of the bag side flange 126 may define a surface that corresponds with the locking shelf 124 of the body side flange 116 to substantially lock the flanges 116, 126 together once thy are positioned as illustrated in FIGS. 1*a*-1*c* and 2*a*-2*c*.

The substantially locked configuration of the flanges 116, 126 means the flanges 116, 126 are coupled to one another to substantially prevent unintentional uncoupling of the flanges 116, 126. That is to say, the flanges 116, 126 are coupled to one another to resist uncoupling under expected forces such as the user moving around when the corresponding bag has fluid therein. However, a user may be able to overcome the substantially locked configuration using typical human force to separate the flanges 116, 126 from one another to replace the corresponding bag.

The deflectable seal 122 of the body side flange 116 may correspond with an adjacent surface in the recess of the bag side flange 126 to substantially seal the bag side flange 126 and the corresponding to the body side flange 116 positioned around the stoma 112. When the flanges 116, 126 are in the substantially locked configuration, the deflectable seal 122 is positioned against the corresponding surface of the bag side flange 126 and thereby seals the flanges 116, 126 to one another about the opening 120.

In one aspect of this disclosure, the fold of the accordion membrane 108 may extend at least partially towards the bag side flange 126 to be positioned radially inside of the bag side flange 126 when in the retracted configuration of FIG. 1. In this configuration, the fold of the accordion membrane 108 may help keep the bag side flange 126 and corresponding bag properly aligned with the opening 120 when coupled to the body side flange 116.

Referring to FIGS. 2*a*-2*c*, the body side flange 116 is illustrated extended from the bridging ring 106. In this configuration, the fold in the accordion membrane 108 is at least partially unfolded to allow the flanges 116, 126 to be at least partially spaced from the abdomen 102. In the extended position of FIGS. 2*a*-2*c*, the flanges 116, 126 may remain in the sealed configuration with the locking shelf 124 coupled in the recess of the bag side flange 126. However, the extended position of FIG. 2 may allow a user to manipulate the flanges 116, 126 with sufficient force to uncouple them from one another and separate the bag side flange 126 and corresponding bag from the body side flange 116. This allows the bag side flange 126 and bag to be replaced without requiring new adhesive 104 as discussed herein.

Referring now to FIGS. 3*a*-3*c*, 4*a*-4*c*, and 5, another embodiment of a coupling assembly 300 is illustrated. This embodiment may have substantially the same advantages, among others, as the embodiment of FIGS. 1*a*-1*c* and 2*a*-2*c* with several improvements relative thereto. More specifically, this embodiment may utilize a substantially integrated accordion membrane 302 and body side flange 304 for a single integrated element 306. The integrated element 306 may define a locking shelf 310 and a deflectable seal 312 that is configured to lock and seal the integrated element 306 to a bag side flange 314 similar to the embodiment discussed with reference to FIGS. 1*a*-1*c* and 2*a*-2*c*.

In one aspect of the coupling assembly 300, the body side flange 304 and the accordion membrane 302 of the integrated element 306 are formed from substantially the same material in a single manufacturing process. In this configuration, the weld area 118 described in FIGS. 1*a*-1*c* and 2*a*-2*c* wherein the accordion membrane 108 is coupled to the body side flange 116 is unnecessary because the body side flange 304 is formed with the accordion membrane 302. By manufacturing a single integrated element 306, the entire manufacturing step of welding the body side flange 116 to the accordion membrane 108 is eliminated. This reduces manufacturing costs and improves quality control by eliminating the complex manufacturing step required by the coupling assembly 100 of aligning the accordion membrane 108 with the body side flange 116 and welding the separate components together.

The coupling assembly 300 otherwise substantially functions the same as the coupling assembly 100. For example, the integrated component 306 may be coupled to a bridging ring 316 via a weld 318 or the like. The bridging ring 316 may be coupled to an adhesive 320 that is configured to be coupled to a patient's abdominal wall 322. Further, the accordion membrane 302 section of the integrated element 306 may allow the body side flange 304 section of the integrated element 306 to be extended relative to the bridging ring 316 from the retracted position in FIGS. 3*a*-3*c* to an extended position of FIGS. 4*a*-4*c*. Further, the locking shelf 310 and deflectable seal 312 may correspond with an annular recess of the bag side flange 314 to selectively couple and seal the bag side flange 314, and the corresponding bag, to the integrated element 316 and thereby to stoma 112 when the bridging ring 316 is coupled to the abdominal wall 322. In other words, the coupling assembly 300 may function in substantially the same way as the coupling assembly 100 while being more practical to manufacture and providing greater quality control.

Figure 4C:
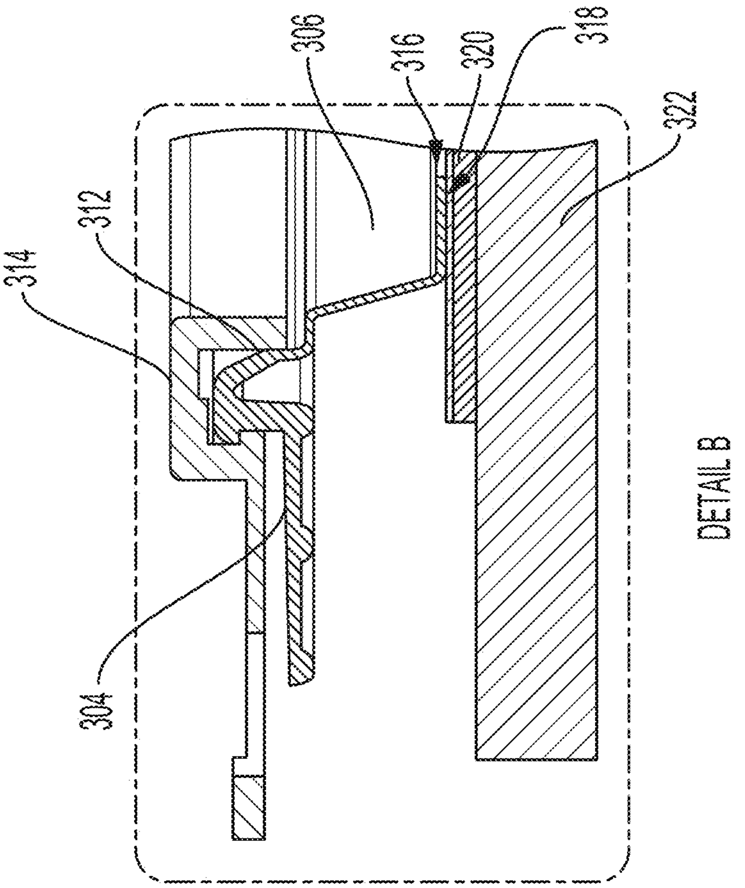
FIG. 4*c* is a detailed view from the cross-sectional view of FIG. 4*b*.
Figure 4A:
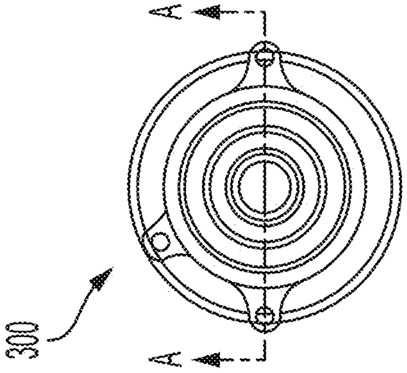
FIG. 4*a* is a top view of the coupling assembly of FIG. 3*a* in an extended position.
Figure 4B:
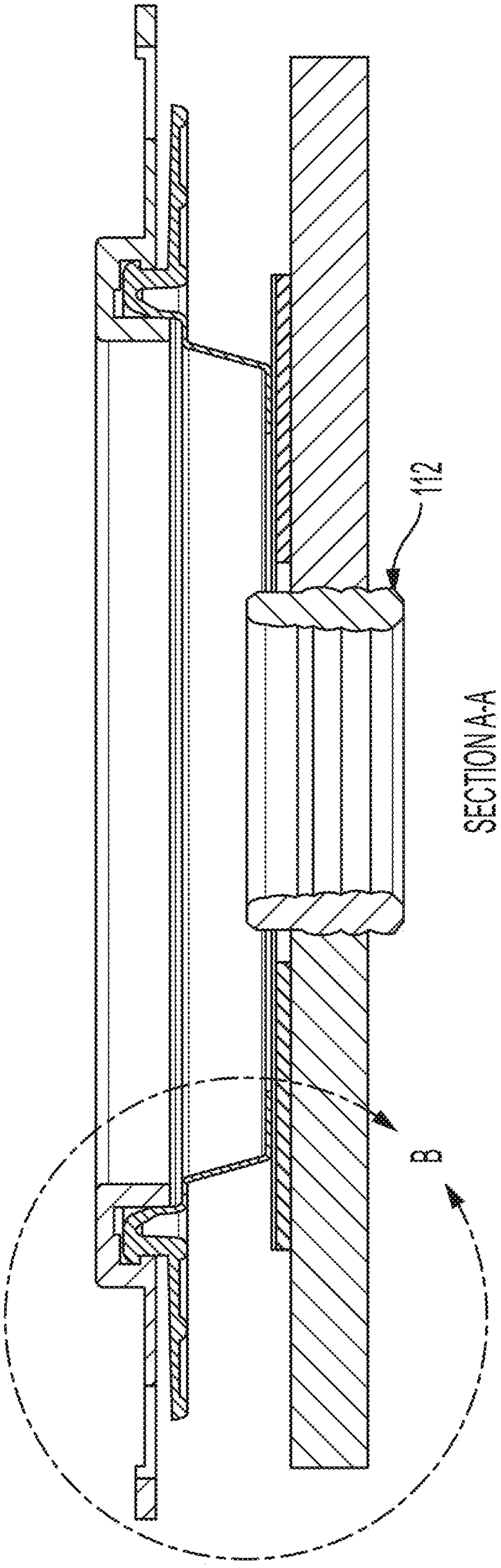
FIG. 4*b* is a cross-sectional view of the coupling assembly of FIG. 4*a;*
Figure 5:
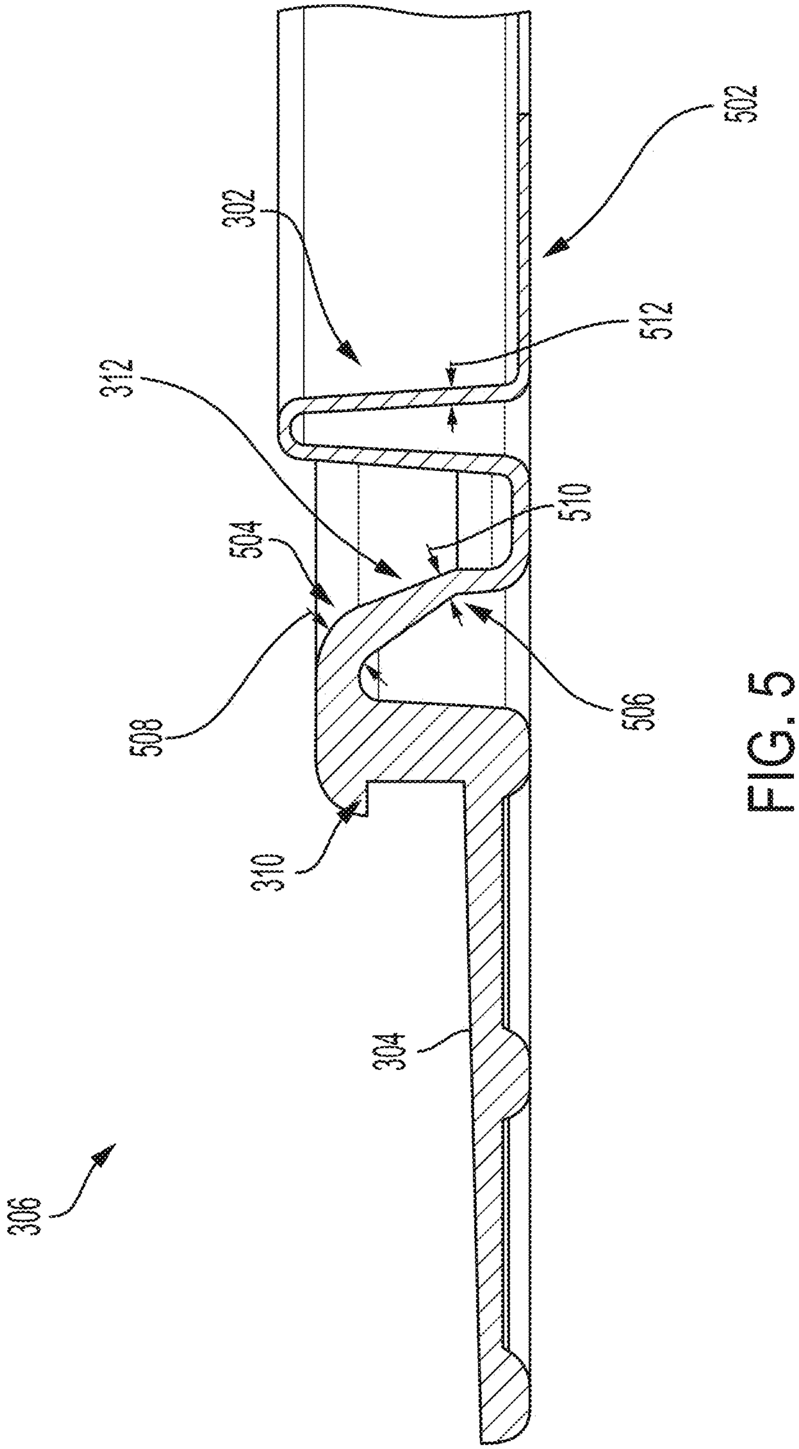
FIG. 5 is a section view of an integrated body side flange and accordion membrane of the coupling assembly of FIGS. 3*a*-4*c*.

Referring now to FIG. 5, an isolated section view of the integrated element 306 is illustrated. As discussed herein, the integrated element 306 may be formed of one seamless material. That is, there are no welds between the accordion membrane 302 and the body side flange 304. Rather, the accordion membrane 302 transitions from a bridging ring section 502 to the deflectable seal 312. The accordion membrane 302 may be formed of a fold of material that allows the integrated element 306 to extend from the retracted position of FIG. 5 to an extended position (as illustrated in FIGS. 4*a*-4*c*) relative to the bridging ring 316.

The deflectable seal 312 may bridge the accordion membrane 302 and the body side flange 304 to couple the sections to one another. Further, the deflectable seal 312 may have a base portion 504 and a sealing portion 506. The cross-section of the deflectable seal 312 may be tapered such that the base portion 504 has a first thickness 508 that is greater than a second thickness 510 at the sealing portion 506. In this configuration, the deflectable seal 312 may be sufficiently rigid to ensure a tight seal against the corresponding bag side flange 314 when coupled thereto and sufficiently pliable to ensure a substantially fluid-tight seal along the bag side flange 314.

The sealing portion 506 may transition directly to the accordion membrane 302 without requiring a seem. In one aspect of this disclosure, the accordion membrane 302 may have a third thickness 512 that is substantially the same as the second thickness 510. However, in other embodiments the third thickness 512 of the accordion membrane 302 may be less than the second thickness of the scaling portion 506. Further still, the third thickness 512 may be greater than the second thickness 510 in certain embodiments contemplated herein.

The base portion 504 may be positioned adjacent to, and formed of the same material, as the locking shelf 310 and remaining portions of the body side flange 304. As such, the entire integrated element 306 may be formed from a single injection molding process. That is to say, the body side flange 304 and accordion membrane 302 may be formed in the single injection-molding process rather than requiring a welding process as necessary for the coupling assembly 100.

In one aspect of this disclosure, the thicknesses 508, 510, 512 may be varied to accommodate different use characteristics. For example, the thickness 512 may be increased to make the coupling assembly 300 more rigid relative to thinner thicknesses 512. This may result in a coupling assembly 300 that resists substantial movement of the ostomy appliance during user movement or full bag conditions. Alternatively, the thickness 512 may be decreased in certain embodiments to provide a coupling assembly 300 that is easier to manipulate into the extended position relative to increased thicknesses at 512. Similarly, the thicknesses 508, 510 of the base portion 504 and sealing portion 506 of the deflectable seal 310 may be altered to affect the scaling properties and case of coupling/uncoupling the bag side flange 314 from the body side flange 304.

Once the thicknesses 508, 510, 512 are determined, a mold may be designed to have a corresponding cavity to create the entire integrated element 306 in a single injection process. That is to say, material may be injected into the mold to form the integrated component 306 without requiring any additional welding or the like. Once the integrated component 306 is formed in the single injection process, the bridging ring section 502 may be coupled to the bridging ring 316 along the weld area 318. While a weld area 318 is discussed herein for coupling the bridging ring 316 to the bridging ring section 502 of the integrated element 306, other coupling techniques are considered herein as well. For example, an adhesive may be used rather than a welding process. The bridging ring 316 may previously or subsequently have the adhesive 320 coupled thereto. At this point, the integrated element 306 and bridging ring 316 may be coupled to a user and the body side flange 304 and corresponding bag may be selectively coupled thereto.

In one aspect of this disclosure, the material injected into the mold to form the integrated element 306 may be a low-density polyethylene. The injection molding-process of the integrated element 306 eliminates the expense and complications of producing a separate, thin-wall membrane from extruded film and then thermoforming and die cutting the film to produce an accordion-membrane component as required in the coupling assembly 100. Also eliminated are the ensuing manufacturing activities of bringing the membrane together with a separate flange and joining them together.

Using an injection-molding process to produce the flexible portion allows wide design latitude. Unlike the film extrusion process where wall thickness must be kept uniform, wall thickness can be optimized for different sizes of products and can be further optimized within a given product size. For example, thicker sectional areas can be provided where stiffness is desired and thinner ones where flexibility is needed as discussed here. The injection molding process allows for designers to create an integrated element 306 having various thicknesses 508, 510, 512, among others, that accommodate the needs of different appliances or users. As such, the present disclosure provides advantages over the prior art regarding the manufacturability of the coupling assembly that allows the integrated element 306 to accommodate the specific needs of the user while being practical to manufacture among other things.

While this disclosure has been described with respect to at least one embodiment, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A process for manufacturing a coupling assembly for an ostomy appliance, comprising:

providing a mold to form an integrated element having a bridging ring section, an accordion membrane, and a body side flange;

injecting a material into the mold to form the integrated element in a single injection process; and removing the integrated element from the mold wherein, the integrated element is configured so the accordion membrane is deformable to allow the body side flange to transition between a retracted position and an extended position relative to the bridging ring section.

2. The process of claim 1, comprising welding the integrated element to a bridging ring.

3. The process of claim 2, further comprising coupling an adhesive to the bridging ring, the adhesive configured to allow a user to selectively couple the bridging ring and corresponding integrated component to the user's abdomen wall.

4. The process of claim 1, further comprising forming a deflectable seal into the integrated element as part of the single injection process.

5. The process of claim 4, wherein the deflectable seal has a base section having a first thickness and a sealing portion with a second thickness that is less than the first thickness.

6. The process of claim 5, further wherein the accordion membrane has a third thickness that is different from the first and second thickness.

7. The process of claim 1, further comprising forming a locking shelf into the integrated element during the single injection process.

8. A method for making a coupling assembly for an ostomy appliance, comprising:

providing a bag side flange configured to be selectively coupled to a deflectable seal about a stoma; and forming an integrated element from a single material, the integrated element having a bridging ring section, an accordion membrane, a body side flange and defining the deflectable seal;

wherein, the integrated element is configured to selectively couple the bag side flange to the deflectable seal of the integrated element so the accordion membrane is deformable to allow the body side flange to transition between a retracted position and an extended position relative to the bridging ring section.

9. The method of claim 8, comprising coupling the integrated element to a bridging ring configured to be selectively coupled to a user.

10. The method of claim 9, further comprising coupling an adhesive to the bridging ring, the adhesive configured to allow a user to selectively couple the bridging ring and corresponding integrated component to the user's abdomen wall.

11. The method of claim 9, further comprising forming a locking shelf into the integrated element during the single injection process.

* * * * *